United States Patent [19]

Boston et al.

[11] Patent Number: 5,552,140
[45] Date of Patent: Sep. 3, 1996

[54] DNA ENCODING A RIBOSOME INACTIVATING PROTEIN

[75] Inventors: Rebecca S. Boston, Raleigh, N.C.; Henry W. Bass, Oakland, Calif.; Gregory R. OBrian, Raleigh, N.C.

[73] Assignee: NorthCarolina State University, Raleigh, N.C.

[21] Appl. No.: 279,996

[22] Filed: Jul. 25, 1994

Related U.S. Application Data

[62] Division of Ser. No. 941,651, Sep. 8, 1992, Pat. No. 5,332,808.

[51] Int. Cl.[6] .............................. C12N 9/24; A61K 38/47; C07K 14/415
[52] U.S. Cl. ...................... 424/94.61; 435/200; 530/376
[58] Field of Search ............................ 435/200; 530/376; 424/94.61

[56] References Cited

U.S. PATENT DOCUMENTS 5,248,606  9/1995  Walsh et al. ........................ 435/240.4

FOREIGN PATENT DOCUMENTS

0466222A1  10/1991  European Pat. Off. .

OTHER PUBLICATIONS

Walsh et al., Characterization and Molecular Cloning of a Proenzyme Form of Ribosome-Inactiving Protein from Maize, *The Journal of Biological Chemistry*, 266:23422–23427 (1991).

Bass et al., A Maize Ribosome-Inactivating Protein is Controlled by the Transcriptional Activator Opaque-2, *The Plant Cell*, 4:225–234 (1992).

*Primary Examiner*—Robert A. Wax
*Assistant Examiner*—Rebecca Prouty
*Attorney, Agent, or Firm*—Bell, Seltzer, Park & Gibson

[57] ABSTRACT

Isolated DNA for a ribosome-inactivating protein found in the tissues of Zea mays is disclosed. The invention also encompasses the protein itself, transgenic plants containing the DNA, DNA constructs for producing the protein, and a host cell containing the DNA.

2 Claims, 9 Drawing Sheets

```
  1         .         .         .         .  *      .         60
CCACTACATATATCTGCAACGAGCGCATCGCCAATTCACAATGCCAATTGCCAGCAACCC
 61         .         .         .         .         .        120
ATCCATACTTTCAGCTGTTGATACAAAAAGAGAAGAGAGAATGGCGGAGCCAAACCCAGA
                                            M  A  E  P  N  P  E
121         .         .         .         .         .        180
GTTGAGTGGTCTTATTACTCAAACAAAGAAGAAAAATATAGTGCCAAAGTTCACCGAAAT
 L  S  G  L  I  T  Q  T  K  K  K  N  I  V  P  K  F  T  E  I
181         .         .         .         .         .        240
CTTCCCCGTGGAGGACACGGCCTACCCTTACAGCGCCTTCATCACCTCCGTCCGGAAAGA
 F  P  V  E  D  T  A  Y  P  Y  S  A  F  I  T  S  V  R  K  E
241         .         .         .         .         .        300
AGTGATCAAATACTGCACCAACCATACAGGCATCGTCCAGCCCGTGCTGCCGCTGGAGAA
 V  I  K  Y  C  T  N  H  T  G  I  V  Q  P  V  L  P  L  E  K
301         .         .         .         .         .        360
GAATGTCCCCGAGCTCTGGTTCTACACCGAGCTCAAAACGAAGACCAGGTCCATCACGCT
 N  V  P  E  L  W  F  Y  T  E  L  K  T  K  T  R  S  I  T  L
361         .         .         .         .         .        420
CGCCATACGTATGGACAACCTCTACCTGGTCGGCTTCAGGACCCCCGGCGGGGTGTGGTG
 A  I  R  M  D  N  L  Y  L  V  G  F  R  T  P  G  G  V  W  W
421         .         .         .         .         .        480
GGAGTTCGGCAAGGACGGCGACACCCACCTCCTCGACGACAACGCCAAGTGGCTCGGCTT
 E  F  G  K  D  G  D  T  H  L  L  D  D  N  A  K  W  L  G  F
481         .         .         .         .         .        540
TGGCGGCCGGTACCAGGACCTCATCGGCAGTAAGGGCCTGGAGACCGTCACCATGGGCCG
 G  G  R  Y  Q  D  L  I  G  S  K  G  L  E  T  V  T  M  G  R
541         .         .         .         .         .        600
TGCCGAAATGACCACGGCCGTCAACTACCTGGCGAAGAAGACGACGACGACACTAGCAGA
 A  E  M  T  T  A  V  N  Y  L  A  K  K  T  T  T  T  L  A  E
601         .         .         .         .         .        660
GGCGGCCGAGGAGGAGGAGGAGCTGCTGCTGCTGCAGGCAGCGGCTGACCCCAAAGCCGA
 A  A  E  E  E  E  E  L  L  L  L  Q  A  A  A  D  P  K  A  E
661         .         .         .         .         .        720
GGAGAAGAGCAACCTGGCGAAGCTAGTGATCATGGTATGCGAGGGGCTGCGGTTCTTCAC
 E  K  S  N  L  A  K  L  V  I  M  V  C  E  G  L  R  F  F  T
721         .         .         .         .         .        780
CGTGTCCCGCAAGGTAGACGAGGGGTTCAAGAAGCCGCAAGCGGTGACCATATCGGCGCT
 V  S  R  K  V  D  E  G  F  K  K  P  Q  A  V  T  I  S  A  L
781         .         .         .         .         .        840
GGAGGGGAAGCAGGTGCAGAAATGGGACAGGATCTCGAAAGCCGTCTTCAGGTGGGCCGT
 E  G  K  Q  V  Q  K  W  D  R  I  S  K  A  V  F  R  W  A  V
841         .         .         .         .         .        900
CGACCCGACCGCTGAGATCCCCGACATGAAGGATCTTGGCATCAAAGATAAAAACGCAGC
 D  P  T  A  E  I  P  D  M  K  D  L  G  I  K  D  K  N  A  A
901         .         .         .         .         .        960
AGCGCAGATCGTTGCGCTCGTTAAGGACCAAAACTAGTACTGCTGCTACTACGTATG
 A  Q  I  V  A  L  V  K  D  Q  N  *
960         .         .         .         .         .       1020
AGAACAAGGAGGAGTTCTCTGATGATGATACACACATCAAGACTTGTTTGTTGCTCTACT
```

FIG. 3.

```
       1                                                                    60
RIP2   MAEPNPELSGLITQT KKKNIVPKFTEIFPV EDTAYP...YSAFIT SVRKEVIKYCTNHTG
RIP1   MAETNPELSDLMAQT NKK.IVPKFTEIFPV EDVNYP...YSAFIA SVRKDVIKHCTDHKG
BR30           MAAKM AKNVDKPLFTATFNV QASSAD...YATFIA GIRNKLRN..PAHFS
MAVP           APTLETIASLDL NNPTT....YLSFIT NIRTKVA.....DKT
RICA           IFPKQYPTINF TTAGATVQSYTNFIR AVRGRLTT...GADVR
SHGI           MKIIIFRVLTFFFVI FSVNVVAKEFTLDFS TAKTYVDSLNVIRSA 61                                                                  120
RIP2   IVQPVLP........ L.EKNVPELWFY TE LKT....KTRS..IT LAIRMDNLYLVGFRT
RIP1   IFQPVLP........ P.EKKVPELWFY TE LKT....RTSS..IT LAIRMDNLYLVGFRT
BR30   HNRPVLP........ PVEPNVPPSRWFHVV LKA....SPTSAGLT LAIRADNIYLEGFKS
MAVP   KTEQKIS........ ...KTFTQRYSYID LIV....SST.QKIT LAIDMADLYVLGYSD
RICA   HDIPVLP........ NRVGLPINQRFILVE LSN....HAE.LSVT LALDVTNAYVVGYR.
SHGI   IGTPLQTISSGGTSL LMIDSGTGDNLFAVD VRGIDPEEGRFNNLR LIVERNNLYVTGFVN 121                                                                 180
RIP2   PGG.....VWWEFGK DGDTHLLDDNAK... ...WLGFGGRYQDLI GSKG.L..ETVTMGRA
RIP1   PGG.....VWWEFGK AGDTHLLGDNPR... ...WLGFGGRYQDLI GNKG.L..ETVTMGRA
BR30   SDG.....TWWEL.. ...TPGLIPGAT... ...YVGFGGTYRDLL GDTDKL.TNVALGRQ
MAVP   IANNKGRAFFFKDVT EAVANNFFPGATGT. NRIKLTFTGSYGDLE K.NGGL......RK
RICA   .AGNS...AYFFHPDN QEDAEAITHLFTDVQ NRYTFAFGGNYDRLE QLAGNLRENIELGNG
SHGI   RTNN....VFYRFAD ......FSHVTFPGT TAVTLSGDSSYTTLQ RVAGISRTGMQINRH 181                                                                 240
RIP2   EMTTAVNYLAKKTTT TLAEAAE........ EEEELLLLQAAADPK AEEKSNLAKLVIMVC
RIP1   EMTRAVNDLAKKKKM ATLEEEEVQMQMQMP EAAELAAAAAAADPQ ADTKSKLVKLVVMVC
BR30   QLADAVTALHGRTK. ............ ......ADKPSGPKQ QQAREAVTTLLLMVN
MAVP   DNPLGIFRLENSIVN I........ ......Y...GKAGDVK KQAKFFLLA..IQMVS
RICA   PLEEAISAL...... ............ ......YYYSTGGTQLP TLARSFIIC.IQMIS
SHGI   SLTTSYLDL...... ............ ......MSHSGTSLT QSVARAMLRFVTVTA

300
RIP2   EGLRFFTVSRKVDEG FKKPQAV.....TIS ALEGKQVQKWDRISK AVFRWAVDP.....T
RIP1   EGLRFNTVSRTVDAG FNSQHGV......TLT VTQGKQVQKWDRISK AAFEWADHP.....T
BR30   EATRFQTVSGFV.AG LLHPKAVEKKSGKIG NEMKAQVNGWQDLSA ALLKTDVKPPPGKSP
MAVP   EAARFKYISDKIPSE .KYE.EVTVDEYMTA LE.....NNWAKLST AVYNSKPSTTTATKC
RICA   EAARFQYIEGEMRTR IRYNRRSAPDPSVIT LE......NSWGRLST AIQESNQC...AFAS
SHGI   EALRFRQIQRGFRTT L...DDLSGRSYVMT AEDVDLTLNWGRLSS VLPDYHGQ.......

301                                                                 360
RIP2   AEIPDMKDLGIKDKN AAAQ...IVALVKDQ N*
RIP1   AVIPDMQKLGIKDKN EAAR...IVALVKNQ TTAAAAAATAASADN DDDEA*
BR30   AKFAPIEKMGVRTAV QAANTLGILLLFVEVP GGLTVAKALELFHAS GGK*
MAVP   QLATSPVTISPWIFK TVEEIKLVWGLL... .....KSS*
RICA   PIQLQRRNGSKFSVY DVSILIPIIALMVYR CAPPPSSQF
SHGI   ....DSVRVGRISFG SINAILGSVALILNC HHHASRVARMASDEF PSMCPADGRVRGITH
```

DNA ENCODING A RIBOSOME INACTIVATING PROTEIN

This application is a divisional of prior application Ser. No. 07/941,651, filed Sep. 8, 1992, the disclosure of which is incorporated by reference herein in its entirety, now U.S. Pat. No. 5,332,808.

FIELD OF THE INVENTION

This invention relates generally to a gene which encodes a protein which inactivates ribosomal activity, and relates more specifically to a gene which encodes a such a protein found in the tissues of Zea mays.

BACKGROUND OF THE INVENTION

Ribosome-inactivating proteins (RIPs) comprise a large group of toxic proteins widely distributed among the plant kingdom. RIPs are most active against nonplant, eukaryotic ribosomes, although activity against prokaryotic ribosomes has been reported. See, e.g., Stirpe et al., *Biochem. J.* 262:1001–1002 (1989). RIPs inactivate ribosomes by enzymatically attacking the 60S subunit of eukaryotic ribosomes and irreversibly modifying its large ribosomal RNA (rRNA). Barbieri et al., *Cancer Surveys* 1:129–141 (1982). This modification results from a specific RNA N-glycosidase activity that depurinates a single adenine found in a universally conserved loop of the large rRNA ($A^{4324}$), See Endo et al., *J. Biol. Chem.* 262:8128–8130 (1987); Endo et al., *J. Biol Chem.* 262:5908–5012 (1987)).

Given the large number of RIPs described in the literature, relatively few RIP genes have been isolated and characterized. Characterization of the maize seed pro-RIP was first reported by Soave et al., *Cell* 27:403–410 (1981) prior to its identification as a RIP. EPO Publication No. 0 466 222 A1 discloses a RIP ("RIP1") produced in the kernels of maize in an inactive form which is activated by the cleaving of an internal peptide. The product is a two-chain active peptide moiety comprising a 16.5 kDa fragment of 169 amino acids and an 8.5 kDa fragment 107 amino acids; the dispensable region comprises 35 amino acids. The gene for the RIP1 maps to position 10 on the long arm of chromosome 8. The protein has been found only in the kernel and germinating seeds of maize. Bass et al., *Plant Cell* 4:225–234 (1992) disclose a cDNA of the RIP1 gene. The protein coded for is highly homologous to RIP1: it has a dispensable internal region; the first fragment varies from RIP1 by only 8 amino acids; and the second fragment is identical to RIP1.

SUMMARY OF THE INVENTION

A first aspect of the present invention is isolated DNA which encodes a ribosome-inactivating protein ("RIP"). The DNA is selected from the group consisting of: (a) isolated DNA having the sequence given herein as SEQ ID NO:1; (b) isolated DNA which is at least 80 percent homologous to the isolated DNA of (a) above and encodes a RIP, and which hybridizes to an oligonucleotide probe, which probe hybridizes to isolated DNA of the sequence given herein as ID SEQ NO:3, but which probe does not hybridize to DNA of the sequence given herein as ID SEQ NO:5; and (c) isolated DNAs differing from the isolated DNAs of (a) and (b) above in nucleotide sequence due to the degeneracy of the genetic code, and which encode a RIP. The DNA preferably encodes a Zea RIP.

A second aspect of the invention is a recombinant DNA comprising vector DNA and a DNA as described in (a)–(c) above. Preferably, the recombinant DNA resides in a host cell suitable for transcription and translation.

A third aspect of the invention is an oligonucleotide probe which selectively hybridizes to isolated DNA having the sequence given herein as SEQ ID NO:3, but which is not capable of hybridizing to isolated DNA having the sequence given herein as SEQ ID NO:5.

A fourth aspect of the invention is a RIP encoded for by DNA as defined in (a)–(c) above. A preferred use for the protein is in an agricultural agent which comprises the RIP and a suitable agricultural carrier.

A fifth aspect of the invention is a transgenic plant comprising a promoter operable in the cells of the plant and DNA as described above which is operatively associated with the promoter.

BRIEF DESCRIPTION OF THE DRAWINGS

FIG. 3 is a nucleotide and deduced amino acid sequence of a maize RIP2 genomic clone. The sequence corresponding to the coding region and nearby flanking regions is shown. The deduced amino acid sequence of RIP2 is indicated below the DNA sequence, and the start and stop codons are printed in bold type. A putative TATA box beginning at position 5 is double underlined. An asterisk (*) marks the putative transcription start site.

FIG. 4 is a comparison of primary structures of RIPs. RIP2, RIP1, BR30, and MAVP denote amino acid sequences of plant type 1 RIPs derived from the maize pRIP2-B6 genomic clone; the maize seed proRIP cDNA, ZmcRIP-9; the barley seed RIP cDNA, BR30; and the Mirabilis antiviral protein cDNA (MAP), respectively. RICA and SHGI denote amino acid sequences derived from the cDNA for the A-chain of castor bean ricin (a type 2 RIP), and the genomic clone for the type 1 shiga toxin (a prokaryotic RIP) from

Figure 1:
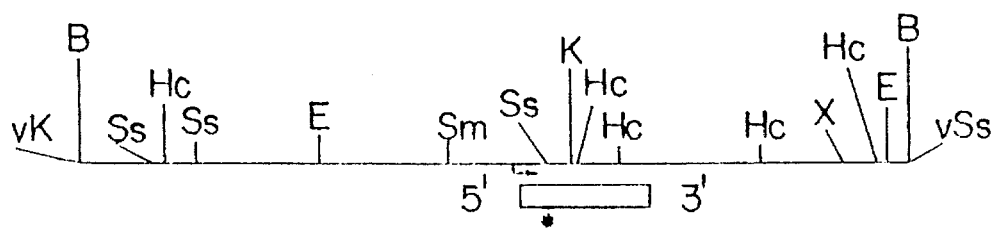
FIG. 1 is a restriction map of plasmid pRIP2-B6. The restriction map of an internal BamHI fragment from a lambdaRIP2 subclone was determined by electrophoretic analysis of digested DNA. The sites shown and their positions (in kb) relative to the first BamHI site are BamHI (B, 0, 6.26), EcoRI (E, 1.8, 6.26), HincII (Hc, 0.63, 3.8, 4.1, 5.15, 6.0), KpnI (K, 3.73), SmaI (SmaI 2.79), SstI (Ss, 0.52, 0.87, 3.58), XbaI (X, 5.75). Of those tested only XhoI is not present within the subclone. Plasmid vector sites from the polylinker of pBluescript (KS/+) shown for orientation are KpnI (vK, –0.06) and SstI (Vs, 6.30). The coding region predicted from sequence analysis is shown by an open box with the orientation of the transcript (5', 3') indicated. Also shown are the positions of the predicted transcriptional initiation site (bent arrow), and the location of the oligonucleotide used for primer extension reactions (*). The positions of subclones used for synthetic RNA production (PS), or probes (5'800, RMA89) are shown.
Figure 2:
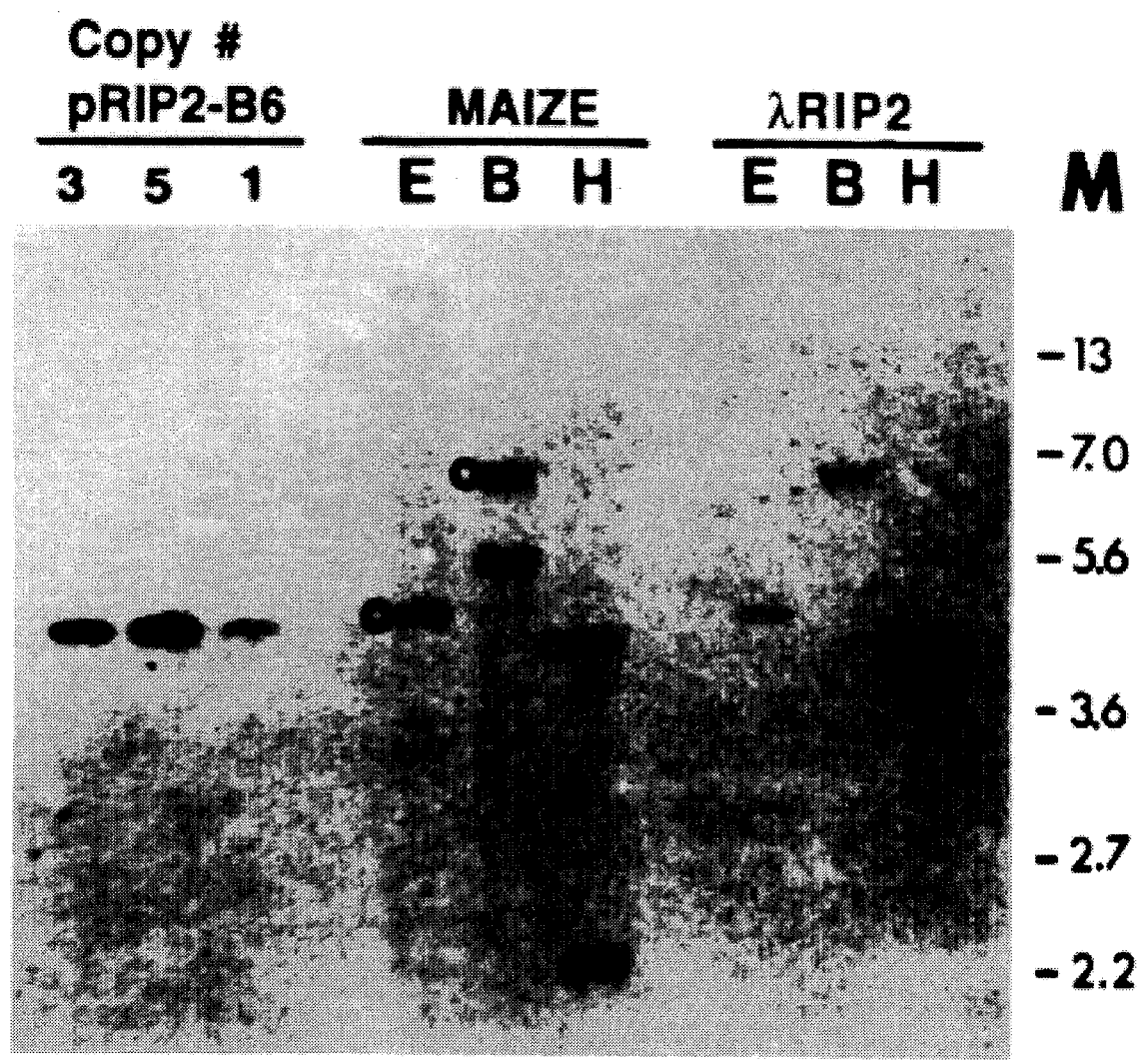
FIG. 2 is a Southern blot analysis of the Maize RIP2 gene. DNA from pRIP2-B6 (Copy #) was digested with EcoRI. DNA from genomic clone lambdaRIP2 (lambdaRIP2) or maize DNA from inbred W64A (Maize) was digested with EcoRI (E), BamHI (B), or HindIII (H). The DNAs on the filter were hybridized at $T_m$–32° C. with a $^{32}$P-labeled RIP1 cDNA (ZmcRIP-3). Copy number reconstructions were based on a maize haploid genome size of 5.3 pg. Molecular weight markers (M) are indicated at right in kb. Bands from maize DNA corresponding to those from lambdaRIP2 are marked with circles (o).

*Shigella dysenteriae*. Sequences were multiply aligned by introduction of gaps ( . . . ) to maximize similarity. The ricin A-chain and MAP start at residues that reflect cotranslational processing points. Similarly, COOH-terminal residue shown for the ricin A-chains (F) represents that found in the native protein. Bold type indicates an identity among at least 4 of the 5 plant RIP sequences at a given position and open circles indicate invariant residues among plant RIPs. Asterisks (*) denote stop codons and numbers identify positions within the alignment. The central portion of pro-RIP (RIP1) that is absent from the mature RIP is underlined.

FIG. 5 shows the presence of RIP2 RNA in various plant parts. RNA gel blot of equal amounts of total RNA (12 μg, except kernel [5 μg] and synthetic RNA [10ng]) from various sources was incubated with the gene-specific radiolabeled RIP2 fragment, RMA89 (specific activity $1\times10^9$ cpm/μg). RNA was purified from mature tassel that was shedding pollen (1), immature preemerged tassel (2), mature silk (3), husk (4), greenhouse-grown leaf (5), field-grown leaf (6), seedling shoot (7), prop roots (8), BMS suspension culture (9), endosperm suspension culture (10), opaque-2 20 DAP kernel (14), or normal 20 DAP kernel (15). Synthetic RNA was made from a cloned RIP1 cDNA (13) or a cloned RIP2 genomic DNA (12). The hybridization was carried out at Tm−8° C. and the filter was exposed for 430 h at −80° C. with an intensifying screen. The positions of RIP2 RNA (arrow), and the large (1R−) and small (sR−) ribosomal RNA are indicated at left.

FIG. 6 shows the presence of RIP2 and RIP1RNA during opaque-2 mutant kernel development by an RNA gel blot of equal amounts of total RNA (10 μg) from developing opaque-2 kernels. The age of the ear at the time of harvest is indicated at the top. A HindIII-SstI fragment from the coding region of a RIP1 cDNA was radiolabeled to a specific activity of $2\times10^9$ cpm/μg and incubated with the RNA at $T_m$−32° C. (RIP). RIP1RNA (−1) and RIP2 RNA (−2) bands are indicated at right. The lower panel is a duplicate gel visualized by acridine orange staining.

FIG. 7 shows the optimization of a primer extension assay. Primer extension products were purified, fractionated, and visualized by autoradiography. Reactions consisted of $5\times10^3$ cpm end-labeled oligonucleotide plus 0.5 ng synthetic RNA (RIP2, RIP1), 10 μg tRNA (tRNA), 5 μg BMV RNA (BMV RNA), or 30 μg total RNA from maize (20 DAP kernel, Endosperm s.c., or BMS s.c.). Additional reaction specifications are described in Example 9. Experimental variables are listed. Lanes not specifying temperature or time consisted of 45° C. 60 min reverse transcription reactions. Molecular weight markers (M) are indicated at right in nt.

FIG. 8 shows the results of a primer extension analysis of maize RNAs. Primer extension reactions were carried out and visualized as described in FIG. 4.7. Reverse transcription reaction conditions employed for all samples were 37° C. 60 min. Headings above the lanes indicate the sources of RNA. Molecular weight markers (M) are indicated at right in nt.

FIG. 9 shows the results of an aniline cleavage assay for RIP activity of synthetic RIP2 RNA translation products. RNA isolated from rabbit reticulocyte translation extracts (40 μL reactions per treatment) was separated on a 4.5% denaturing gel and visualized by ethidium bromide staining. Translation reactions received BMV RNA (BMV), gelonin (GLN), RIP2 synthetic RNA-sense strand (R2+), or RIP2 synthetic RNA-antisense strand (R2−). Aliquots of purified RNA were prepared for electrophoresis (lanes with odd #s) or treated with aniline (lanes with even #s) before electrophoresis. The arrow indicates the aniline cleavage product diagnostic for RIP-modified RNAs.

DETAILED DESCRIPTION OF THE INVENTION

As noted above, ribosome-inactivating proteins are proteins which inactivate or severely reduce the activity of ribosomes, in particular nonplant eukaryotic ribosomes, although inactivation of prokaryotes and viruses has been observed. This activity makes these proteins useful in a variety of ways. They can be used to fight pests in crops, either as an applied pesticide formulation or by incorporation into the genome of the plant. They also have utility as, among others, immunotoxins and anti-viral agents. Further, they are useful in vitro to arrest protein translation from RNA in biochemical assays where a precise termination of the reaction is desired.

1. DNA Encoding Ribosomal Inactivating Proteins.

In general, and as explained in greater detail below, DNA encoding RIPs of the invention includes DNA which is 80 percent homologous or more with DNA having the sequence given herein as SEQ ID NO:1. With respect to the protein, DNA encoding this RIP encode a protein which, in amino acid content, is about 80 percent homologous or more, or preferably about 85% homologous or more, with the protein having the amino acid sequence given herein as SEQ ID NO:2. Determinations of homology are made with the two sequences (nucleic acid or amino acid) aligned for maximum matching. Gaps in either of the two sequences being matched are allowed in maximizing matching. Gaps lengths of 10 or less are preferred, gap lengths of 5 or less are more preferred, and gap lengths of 2 or less still more preferred.

The DNA can be recovered from within the cells of it natural host, or it can be synthesized directly. Exemplary are direct syntheses are chemical syntheses, which include manual procedures, such as the phosphodiester or phosphotriester methods, see Caruthers, in *Methodology of DNA and RNA* (Weisman ed. 1983), and automated procedures. Also, the DNA may be constructed by standard techniques of annealing and ligating fragments or by other methods. Also exemplary are cloning procedures discussed in section 3 below.

The present invention also includes DNA sequences which hybridize to oligonucleotide probes which hybridize to DNA defined by SEQ ID NO:3 but do not hybridize to DNA defined by SEQ ID NO:5 and which code on expression for a RIP. Conditions under which such sequences will so hybridize can be determined in a routine manner. For example, hybridization of such sequences may be carried out under conditions of reduced stringency or even stringent conditions (e.g., conditions represented by a wash stringency of 0.3M NaCl, 1, 0.03M sodium citrate, 0.1% SDS at 60° C. or even 70° C. to DNA having the sequence given as SEQ ID NO:1 herein in a standard in situ or filter hybridization assay. See J. Sambrook et al., Molecular Cloning, A Laboratory Manual (2d Ed. 1989)(Cold Spring Harbor Laboratory)). In general, such sequences will be at least 80 percent homologous, 85 percent homologous, 90 percent homologous, or even 95 percent homologous or more with the sequence given herein as SEQ ID NO:1. Determinations of homology are made with the two sequences aligned for maximum matching. Gaps in either of the two sequences being matched are allowed in maximizing matching. Gap lengths of 10 or less are preferred, gap lengths of 5 or less are more preferred, and gap lengths of 2 or less still more preferred. Those skilled in this art will appreciate that a DNA sequence of this sort will encode a RIP which has portions of its amino acid sequence which are equivalent to amino acid sequences obtained directly from nature and will exhibit essentially biological activity.

Promoters employed in carrying out the present invention may be active in numerous different plant tissues. SEQ ID NO:1 includes therein a promoter region for the RIP gene. This promoter region can be DNA which controls the expression of the RIP gene and which is 40, 50, 60, or even 70 percent homologous with the promoter region of SEQ ID NO:1. In addition, several plant and viral genes are actively expressed in multiple tissues. Exemplary genes encode the B-subunit of the mitochondrial ATPase complex, B-tubulin, actin, acetohydroxyacid synthase, and the 35S RNA of cauliflower mosaic virus.

2. Ribosomal Inactivating Proteins.

RIPs encompassed by the present invention include proteins having the amino acid sequence given as ID SEQ NO:2 and proteins homologous to, and having essentially the same biological properties as, the protein disclosed herein as SEQ ID NO:2. This definition is intended to encompass natural allelic variations in the protein, although at least one embodiment has been found to be nonallelic. It will be appreciated that the amino acid sequence need not be identical to that of SEQ ID NO:2; for the purposes of this invention, the amino acid sequence may be at least 80 percent, 85 percent, 90 percent, or even 95 percent homologous or more with the protein of SEQ ID NO:2 to retain its biological activity. General categories of potentially equivalent amino acids include, but are not limited to: glutamic acid and aspartic acid; lysine, arginine, and histidine; alanine, valine, leucine, and isoleucine; asparagine and glutamine; threonine and serine; phenylalanine, tyrosine and tryptophan; and glycine and alanine. These proteins can be produced by recombinant methods as described below, by synthesis of the RIP from its constituent amino acids, or other methods.

The RIP of the present invention can be produced by standard techniques for isolating proteins from biological systems, such as salt precipitation, column chromatography, immunoaffinity techniques, electrophoresis, recrystallization, centrifugation, and the like. In addition, the RIP can be raised by recombinant techniques, wherein cDNA clones for the DNA sequence encoding the RIP of the present invention are produced, isolated, proliferated, and transferred to a suitable host cell, such as E. coli. In the host cell, the DNA sequence produces the RIP in far greater abundance than that seen in its natural environment.

3. Genetic Engineering of Plants.

DNA constructs, or "transcription cassettes," of the present invention include, 5'-3' in the direction of transcription, a promoter as discussed above and, optionally, a termination sequence including stop signal for RNA polymerase and a polyadenylation signal for polyadenylase (e.g., the nos terminator). All of these regulatory regions should be capable of operating in the cells of the tissue to be transformed. The 3' termination region may be derived from the same gene as the transcriptional initiation region or may be derived from a different gene.

The transcription cassette may be provided in a DNA construct which also has at least one replication system. For convenience, it is common to have a replication system functional in *Escherichia* coli, such as ColE1, pSC101, pACYC184, or the like. In this manner, at each stage after each manipulation, the resulting construct may be cloned, sequenced, and the correctness of the manipulation determined. In addition, or in place of the E. coli replication system, a broad host range replication system may be employed, such as the replication systems of the P-1 incompatibility plasmids, e.g., pRK290. In addition to the replication system, there will frequently be at least one marker present, which may be useful in one or more hosts, or different markers for individual hosts. That is, one marker may be employed for selection in a prokaryotic host, while another marker may be employed for selection in a eukaryotic host, particularly the plant host. The markers may be protection against a biocide, such as antibiotics, toxins, heavy metals, or the like; provide complimentation, by imparting prototrophy to an auxotrophic host: or provide a visible phenotype through the production of a novel compound in the plant. Exemplary genes which may be employed include neomycin phosphotransferase (NPTII), hygromycin phosphotransferase (HPT), chloramphenicol acetyltransferase (CAT), nitrilase, and the gentamicin resistance gene. For plant host selection, non-limiting examples of suitable markers are luciferase, providing visible light production, NPTII, providing kanamycin resistance or G418 resistance, HPT, providing hygromycin resistance, phosphinothricin acetyl transferase encoded by the bar gene of streptomyces provides resistance to bialophos and BASTA, and the mutated aroA gene, providing glyphosate resistance.

The various fragments comprising the various constructs, transcription cassettes, markers, and the like may be introduced consecutively by restriction enzyme cleavage of an appropriate replication system, and insertion of the particular construct or fragment into the available site. After ligation and cloning the DNA construct may be isolated for further manipulation. All of these techniques are amply exemplified in the literature and find particular exemplification in Maniatis et al., supra.

Vectors which may be used to transform plant tissue with DNA constructs of the present invention include both *Agrobacterium* vectors and ballistic vectors, as well as vectors suitable for DNA-mediated transformation.

Methods of making recombinant ribosome-inactivating plants of the invention, in general, involve providing a plant cell capable of regeneration (the plant cell typically residing in a tissue capable of regeneration). The plant cell is then transformed with a DNA construct comprising a transcription cassette of the present invention (as described herein) and a recombinant ribosome-inactivating plant regenerated from the transformed plant cell. As explained below, the transforming step is carried out by bombarding the plant cell with microparticles carrying the transcription cassette, by infecting the cell with an Agrobacterium *tumefaciens* containing a Ti plasmid carrying the transcription cassette, electroporation of immature embryos, or any other technique suitable for the production of a transgenic plant.

Numerous *Agrobacterium* vector systems useful in carrying out the present invention are known. For example, U.S. Pat. No. 4,459,355 discloses a method for transforming susceptible plants, including dicots, with an *Agrobacterium* strain containing the Ti plasmid. The transformation of woody plants with an *Agrobacterium* vector is disclosed in U.S. Pat. No. 4,795,855. Further, U.S. Pat. No. 4,940,838 to Schilperoort et el. discloses a binary *Agrobacterium* vector (i.e., one in which the *Agrobacterium* contains one plasmid having the vir region of a Ti plasmid but no T region, and a second plasmid having a T region but no vir region) useful in carrying out the present invention.

Microparticles carrying a DNA construct of the present invention, which microparticle is suitable for the ballistic transformation of a plant cell, are also useful for making transformed plants of the present invention. The microparticle is propelled into a plant cell to produce a transformed plant cell, and a plant is regenerated from the transformed plant cell. Any suitable ballistic cell transformation methodology and apparatus can be used in practicing the present invention. Exemplary apparatus and procedures are disclosed in Sanford and Wolf, U.S. Pat. No. 4,945,050, and in Christou et al., U.S. Pat. No. 5,015,580. When using ballistic transformation procedures, the transcription cassette may be incorporated into a plasmid capable of replicating in the cell to be transformed. Examples of microparticles suitable for use in such systems include 1 to 5 μm gold spheres. The DNA construct may be deposited on the microparticle by any suitable technique, such as by precipitation.

Plant species may be transformed with the DNA construct of the present invention by the DNA-mediated transformation of plant cell protoplasts and subsequent regeneration of the plant from the transformed protoplasts in accordance with procedures well known in the art.

Any plant tissue capable of subsequent clonal propagation, whether by organogenesis or embryogenesis, may be transformed with a vector of the present invention. The term "organogenesis," as used herein, means a process by which shoots and roots are developed sequentially from meristematic centers; the term "embryogenesis," as used herein, means a process by which shoots and roots develop together in a concerted fashion (not sequentially), whether from somatic cells or gametes. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristems, axillary buds, and root meristems), and induced meristem tissue (e.g., cotyledon meristem and hypocotyl meristem).

Plants of the present invention may take a variety of forms. The plants may be chimeras of transformed cells and non-transformed cells; the plants may be clonal transformants (e.g., all cells transformed to contain the transcription cassette); the plants may comprise grafts of transformed and untransformed tissues (e.g., a transformed root stock grafted to an untransformed scion in citrus species). The transformed plants may be propagated by a variety of means, such as by clonal propagation or classical breeding techniques. For example, first generation (or T1) transformed plants may be selfed to give homozygous second generation (or T2) transformed plants, and the T2 plants further propagated through classical breeding techniques. A dominant selectable marker (such as npt II) can be associated with the transcription cassette to assist in breeding.

Plants which may be transformed by the techniques described above include species of the following genera (with exemplary species in parentheses): *Zea mays* (maize); *Gossypium hirstium* (cotton); *Nicotinia tabacura* (tobacco); *Solanum tuberosum* (potato); *Glycine max* (soybean); *Arachis hypogaea* (peanut); *Dendranthema* spp. (chrysanthemum); *Brassica napus* (oil-seed rape); *Sorghum bicolor* (sorghum); *Triticum aestivum* (wheat); *Oryza sativa* (rice) and *Lycopersicon esculentum* (tomato). Particular pathogens which can be resisted by the present invention include: *Phytophthora parasitica* var. nicotinae (root-infecting blank shank), *Alternaria alternata* (foliar-infecting brownspot); *Fusarium oxysporum*; *Fusarium moniliforme*; *Rhizoctonia solani*; *Aspergillus flavus*; *Diabrotica virgifera* (Western corn root-worm); *Callosobruchus maculatus* (cowpea seed weevil); *Anthonomus grandis* (cotton bollweevil); and *Meloidogyne incognita* (root-knot nematode).

The present invention is explained in greater detail in the following non-limiting examples. These examples are provided so that the invention can be more completely understood and are not to be construed as restrictive of the invention. Amino acid sequences disclosed herein are presented in the amino to carboxyl direction, from left to right. The amino and carboxyl groups are not presented in the sequence. Nucleotide sequences are presented herein by single strand only, in the 5' to 3' direction, from left to right.

In the Examples, "kb" means kilobases, "$A_{260}$" means light absorption at 260 nanometers, "μg" means micrograms, "Ml" means milliliters, "Mm" means millimoles, "° C.", means degree Centigrade, "L" means liters, "bp" means base pairs, "nt" means nucleotide, "h" means hours, "ng" means nanograms, "CDNA" means carrier DNA, and "min" means minutes. In the Figures showing amino acid sequences, "A" means adenine, "T" means thymine, "G" means guanine, and "C" means cytosine". In the Figures showing protein sequences, "A" means alanine, "M" means methionine, "E" means glutamic acid, "P" means proline, "N" means asparagine, "L" means leucine, "S" means serine, "G" means glycine, "I" means isoleucine, "T" means threonine, "Q" means glutamine, "K" means lysine, "V" means valine, "F" means phenylalanine, "D" means aspartic acid, "Y" means tyrosine, "R" means arginine, "C" means cysteine, "H" means histidine, and "W" means tryptophan.

EXAMPLE 1

Collection and Care of Plant Materials

Maize was grown and harvested as described by Bass et al., (1992) and included 1992 field- or greenhouse-grown plants (Raleigh, N.C.). Tissues were harvested and immediately frozen in liquid nitrogen. Field-grown roots and prop roots were briefly rinsed with water to remove soil before freezing. Black Mexican sweet corn (BMS) suspension culture was obtained from Ciba-Geigy, Corp. Research Triangle Park, N.C., and maintained as described in Green, *Hort. Sci.* 12:131–134 (1977). Endosperm suspension culture was initiated from a hybrid maize line available from North Carolina State University, Raleigh, N.C., and was maintained as described in Shannon, Maize endosperm cultures in *Maize for Biological Research* 397–400 (W. F. Sheridan ed., Grand Forks, N. Dak.: Univ. North Dakota Press, 1982). Cultured cells were collected by filtration through cheesecloth prior to freezing in liquid nitrogen.

EXAMPLE 2

Molecular Cloning of RIP2

A maize (inbred W64A) DNA library in lambdagemll (Promega, Madison Wis.) was constructed and made available by G. J. Wadsworth and J. G. Scandalios (described in Wadsworth et al. *Anal. Biochem.* 172:279–283 (1989). The library, which comprises leaf DNA partially-digested by Sau3A I, was screened by hybridization at Tm–30° C. with a RIP1 cDNA clone (pZmcRIP-3, Bass et al., supra) radiolabeled with 32P-dCTP. A class of cross-hybridizing clones with restriction enzyme patterns similar but not identical to that of the RIP1 gene was repeatedly isolated.

A 6.3 kb Bam HI restriction fragment from a representative member of these clones (lambdaRIP2C6) was subcloned into the Bam HI site of Pbluescript to produce the plasmid designated pRIP2-B6. Suitable subclones of pRIP2-B6 were sequenced by the dideoxynucleotide chain termination method (Sanger et al., *Proc. Natl. Acad. Sci. USA.* 74:5463–5467 (1977)) using the Sequenase™ enzyme.

Sequence analysis was performed with the SeqEd and fragment assembly programs of the Genetics Computer Group software package (GCG, Madison, Wis.). Subclones of pRIP2-B6 were also used for probe preparation and RNA synthesis.

The restriction enzyme map of pRIP2-B6 is presented schematically in FIG. 1. The position of an open reading frame derived from the DNA sequence is indicated in FIG. 1 as an open box. The restriction sites indicated above the line were determined by electrophoretic analysis of restriction fragments.

EXAMPLE 3

Genomic Southern Blot Analysis of Maize RIPs

To identify the maize DNA fragments that corresponded to the lambdaRIP2 clone produced in Example 2, a genomic Southern blot analysis was performed. DNA was isolated from bacteriophage lambdaRIP2 according to the method of Maniatis et al., supra. For DNA from W64A ear shoot material, the method of Zimmer et al., A simple method for the isolation of high molecular weight DNA from individual maize seedlings and tissues, in *Maize for Biological Research* 165–168 (W. F. Sheridan ed., Grand Forks, N. Dak.: Univ. North Dakota Press (1982), was scaled up and followed through the step for proteinase K treatment. DNA was purified from- the resulting solution by centrifugation in CsCl as described by Maniatis et al. supra, and quantified by UV absorbance spectroscopy. DNAs were digested with restriction enzymes, quantified by UV spectroscopy (1.0 $A_{260}$=50 μg/mL), fractionated on a 1% (weight:volume) agarose/TBE gel (TBE is 89 mM tris[hydroxymethyl] aminomethane, 89 mM boric acid, 2 mM EDTA-NaOH; pH=8), and transferred to a nylon membrane (GeneScreen, NEN) by the capillary blotting method of Southern, *J. Mol. Biol.* 98:503–517 (1977). All filter hybridization steps were kept at $T_m$–30° C. The methods of probe preparation hybridization and autoradiography were performed as previously described in Bass et al., supra. Hybridization stringency determinations were based on the formulas described by Casey et al., *Nucleic Acids Res.* 4:1539–1549 (1977) and Wetmur et al., *J. Mol. Biol.* 31:349–370 (1968). The formula used was $T_m$=81.5° C.+16.6×log[salt]+0.41(% G+C) - 650/L. In the formula, L is the average length of the probe in nucleotides.

The results of the analysis are shown in FIG. 2. In order to observe all RIP-like sequences, a radiolabeled maize RIP1 cDNA clone (ZmcRIP-3, Bass et al., supra), was hybridized at moderate stringencies to maize DNA digested with EcoRI, BamHI, or HindIII (lanes E, B, or H, respectively). The blot also contained lanes with lambdaRIP2 DNA (lambdaRIP2 Lanes) digested with the same enzymes to allow correlation of fragments from genomic DNA with restriction fragments from the clone. Only one band per lane was detected from lambdaRIP2. These were determined to be 4.3 kb (lanes E), 6.3 kb (lanes B), and 4.0 kb (lanes H). A corresponding set of bands from maize DNA (Maize) was observed and was indicated with circles (o).

The 6.3 kb BamHI band represents the fragment subcloned as plasmid pRIP2-B6 (FIG. 1). This band also contained the 4.3 kb EcoRI fragment. These results indicated that the lambdaRIP2 DNA had not undergone any major rearrangement during cloning.

In addition to the RIP2 bands, maize contained bands determined to be approximately 18 kb and 30 kb in the EcoRI-digested DNA (Maize section), 5.5 kb in the BamHI digested DNA, and 2.15 kb in the HindIII digested DNA. These fragments were presumed to harbor the RIP1 gene. A copy number reconstruction (copy # pRIP2-B6) was made with EcoRI-digested pRIP2-B6. By comparison with the maize genomic DNA, it was determined that the maize RIP2 sequences (bands marked by o) were present at approximately 1 copy per haploid genome. Because the probe had been made from a full length RIP1 cDNA, the homologous maize bands containing RIP1 showed a stronger hybridization signal than did those containing RIP2. This difference most likely resulted from mismatch of the heterologous RIP1:RIP2 hybrids, especially for the 120 nt 3 min of the RIP1 cDNA coding region. For this reason, an accurate copy number reconstruction can be made for the RIP2 gene but the comparison can not be extended to the RIP1 genes.

EXAMPLE 4

Chromosomal Localization of the RIP2 RFLP Locus

An 800 bp SmaI-SstI restriction fragment from pRIP2-B6 was used as a probe to determine the chromosomal position of RIP2 (FIG. 1, 5'800). The RFLP blots contained maize DNA from two sets of recombinant inbred lines from a permanent mapping population (Burr et al., *Trends Genet.* 7:55–60 (1991)). The probe detected only one restriction fragment that differed in size from one parental line to another. This RFLP was scored and mapped to chromosome 7L between the RFLP loci BNL8.21A and BNL7.61.

EXAMPLE 5

DNA Sequence Determination of a RIP2 Genomic Clone

The sequence of a portion of pRIP2-B6 that showed cross-hybridization with RIP1 cDNA was determined as described in Example 2. This sequence is shown along with the deduced amino acid sequence in FIG. 3. The DNA sequence allowed prediction of an open reading frame of 278 amino acids. No introns were observed, although a corresponding cDNA was not isolated to confirm this. The presumed start (ATG) and stop (TAG) codons are indicated by bold letters. The proportion (68%) of codons specifying C or G in the third position was consistent with the codon usage of cloned maize nuclear genes (Campbell et al., *Plant Physiol.* 92:1–11 (1990)). The putative peptide did not show features of an NH2-terminal signal peptide for synthesis on the ER (Von Heihn, *Nucleic Acids Res.* 14:4683–4690 (1990)). A sequence upstream of the start codon resembling a TATA box is underlined. In comparison with the RIP1 cDNA ( ZmcRIP-9), the DNA identity within the coding region is 83%. This level of similarity drops to 60% in the 100 nt span 5' of the coding region and to 54% in the 130 nt span 3' of the coding region.

Comparative Example A

The amino acid sequence deduced from RIP2 was compared with those of several other RIPs. The sequence alignment is presented in FIG. 4. The RIP2 sequence (RIP2) was aligned with sequences of the maize pro-RIP, ZmcRIP-9 (RIP1); RIP30 (RP30), a type 1 RIP from barley seed; the A-chain of ricin (RICA), a type 2 RIP from castor bean; the Mirabilis antiviral protein or MAP (MAVP), a type 1 RIP from the roots of Mirabilis, and the type I shiga toxin (SHGI), a microbial RIP from *Shigella dysenteriae*. The NH2-terminal residues shown for ricin A-chain and MAP and the COOH-terminal residue shown for the ricin A-chain represent the terminal amino acids found in the native protein (Halling et al. *Nucleic Acids Res.* 13:8019–8033

(1985); Habuka et al., *J. Biol. Chem.* 264:6629–6637 (1989)). The 21 COOH-terminal residues of the shiga toxin did not align with any plant RIPs and are not shown.

RIPs commonly exhibit a low overall homology with each other, but have strict conservation of some residues (Ready et al., *Proteins* 3:53–59 (1988)). A recent display generated with the GCG pileup program for multiple sequence alignment showed 10 positions of invariant residues among the 15 plant RIPs compared (data not shown). The positions of these 10 residues are identified here as open circles (o) above the RIP2 sequence. Five of these invariant residues, Y-119, Y-166, E-241, R-244, and W-295 have been determined to reside in the presumed active site cleft of the ricin A-chain as determined by X-ray crystallography and mutagenesis studies (Montfort et al. *J. Biol. Chem.* 262:5398–5403 (1987); Ready et al., *Proteins* 10:270–278 (1991); Frankel et al., *Mol. Cell. Biol.* 9:415–420 (1989); Katzin et al., *Proteins* 10:251–259 (1991)). Small blocks of homology such as PVLP at 64–67, TLAI at 105–108, and FGG at 157–159 were revealed by highlighting residues identical in 4 of the 5 plant RIPs (FIG. 4), yet the basis for their conservation is unknown.

The maize pro-RIP (line RIP1) undergoes a proteolytic activation that results in removal of amino acids from both termini as well as an internal region (Walsh et al., *J. Biol. Chem.* 266:23422–23427 (1991)). The boundaries of the internal region removed were deduced from direct sequencing of an active RIP preparation, and the region removed is underlined in FIG. 4 (positions 194–220). Interestingly, RIP2 also contained extra amino acids in this region (194–220).

EXAMPLE 7

Expression of the RIP2 gene

To analyze expression of the RIP2 gene, it was first necessary to identify probes that would distinguish between RIP1 and RIP2 transcripts. A gene-specific probe was isolated from an internal 89 bp RmaI restriction fragment of pRIP2-B6 that had identity with only 65% of the nucleotides in the corresponding region of RIP1. The position of this RmaI fragment within pRIP2-B6 is shown in FIG. 1 (RMA89). $T_m-8°$ C. was chosen as the hybridization stringency for probing RNA prepared from various plant parts with radiolabeled RMA89 because at a hybridization stringency of $T_m-8°$ C., sequences with greater than 10% mismatch should not anneal (Bonner et al., *J. Mol. Biol.* 81:123 (1973)).

For the procedure, RNA was isolated from developing kernels as described in Langridge et al., *Planta* 156:166–170 (1982). RNA from non-kernel tissues was isolated by the phenol/SDS method for plant RNA preparation (Ausubel et al., *Current Protocols in Molecular Biology* (N.Y.: Greene Publishing Associates, Wiley-Interscience 1992) modified by the addition of polyvinyl-pyrrolidone and polyvinyl-polypyrrolidone (PVP-360 and PVPP, Sigma Chem. Co., St. Louis, Mo.) to 1% (weight:volume) each in the initial grinding buffer, and the subsequent addition of a LiCl precipitation step (4M LiCl, 4° C., 12 h) following resolubilization of the pellet collected after precipitation by isopropyl alcohol. The RNA was dissolved in 0.1 mL $H_2O$ per gram starting tissue, and was then quantified by UV absorbance spectroscopy using the equation 40 µg/mL=1.0 $A_{260}$ Unit.

Figure 5:
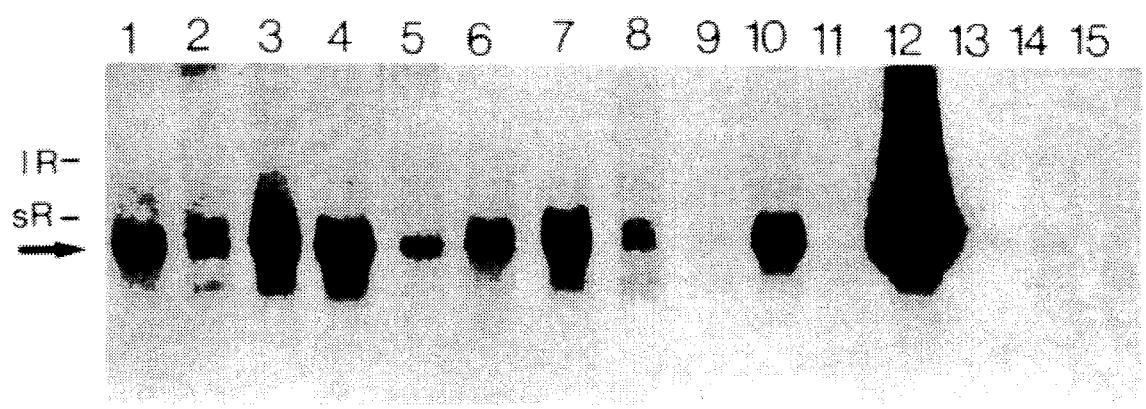

The results of the RNA gel analysis are shown in FIG. 5. A strong signal (arrow) was observed for RNA prepared from tassel (1), silk (3), husk (4), seedling shoot (7), and endosperm suspension culture (10). This signal was not due to RIP1 RNA and likely represented transcripts from the RIP2 gene. This assertion is based on the comparison of internal controls which contained either 10 ng of synthetic RIP2 RNA (12) or 10 ng of synthetic RIP1 RNA (13). These RNAs were sense-strand RNAs produced in vitro. A template for synthetic RNA was made from a subclone of pRIP2-B6. An 864 bp PVU II, Sca I restriction fragment was ligated into the Sma I site of pBluescript. The plasmid was designated pPST7 (5' end adjacent to the T7 promotor in the vector). The plasmid pZmcRIP-3 used for preparation of RNA for RIP1 contained a full-length maize RIP1 cDNA (5' end adjacent to the T3 promoter in Bluescript) and has been described previously by Bass et al., supra (1992). For RNA production from either strand of the cloned RIP2 gene, template plasmids were linearized by restriction enzyme digestion at a single site and transcribed in vitro with T7 or T3 RNA polymerases according to standard procedures. Thus, at the stringency used, the RMA89 probe did not show any detectable hybridization with RIP1 RNA.

In addition to the RIP2 RNA bands, a weaker band (arrow) of the same size was detected in RNA from immature tassel (2), leaf (5,6), and prop root (8). No bands were detected in RNA from a Black Mexican Sweet corn (BMS) suspension culture (9), opaque-2µmutant (14) or normal (15) kernels harvested at 20 DAP. In three lanes an additional band was observed just above the RIP2 RNA band (2, 6, 8). These larger bands may have resulted from the presence of the abundant small rRNA (position indicated as -sR) which appeared to displace the background signal within a lane. Such displacement toward the bottom of the gel would result in a compact band. RNA from prop root (8) and immature tassel showed a faint band below the RIP2 RNA signal. Neither the source nor the significance of this band is known. The data shown indicates that most non-kernel plant parts contained RIP2 RNA.

Additionally, the reason for background signal in some but not all lanes is not known. One possibility could be that the background reflects the variation in the amount of organellar or microbrial RNA present that may be cross hybridizing with trace amounts of radiolabeled E. coli fragments.

The difference in migration of the RIP2 RNA band in the silk RNA (3) coincided with a similar distortion of the entire RNA sample as determined by acridine orange staining of a duplicate gel prepared from the same glyoxalation reaction (data not shown). These distortions were assumed to result from contaminating molecules, possibly polysaccharides, that copurified with the RNA.

EXAMPLE 8

RNA Accumulation Patterns of RIP2 and RIP1 in Developing opaque-2 Kernels

To observe both RIP1 and RIP2 RNA in a single gel blot, an internal radiolabeled RIP1 cDNA fragment was hybridized to kernel RNA at a moderate stringency ($T_m-32°$ C.). RNA from developing opaque-2 kernels was chosen because it had been determined previously that a low level of RIP1 RNA was present at specific developmental stages (Bass et al., supra). The lowered stringency and use of an internal restriction fragment as a probe also guaranteed cross-hybridization with any RIP2 that may also be present.

Figure 6:
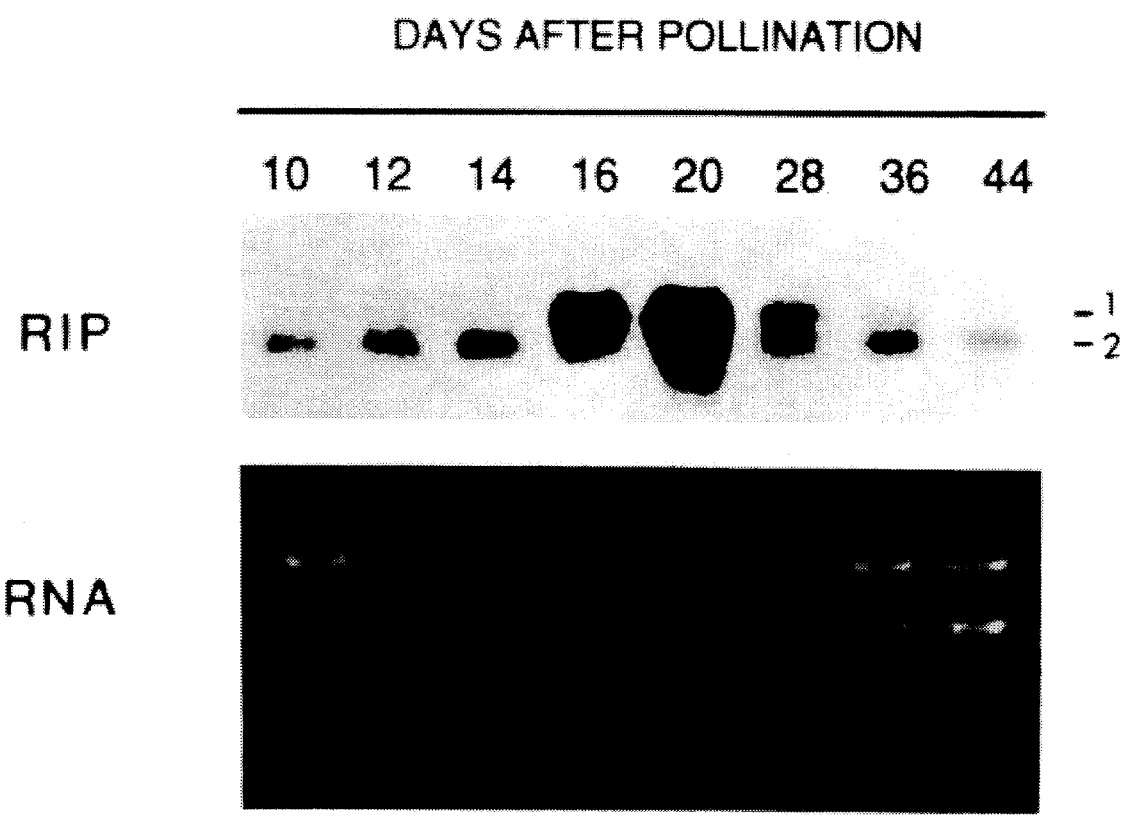

FIG. 6 shows that by this approach, both RIP1 and RIP2 RNA were detected. The upper band (−1) was approximately 1200 nt and determined to be from the RIP1 gene because of its characteristic developmental pattern of being most abundant at 16 and 20 DAP. The lower band of approximately 950 nt (−2) was considered to be RIP2 RNA and was detected in RNA samples from 10, 12, 14, 28, 36 and 44 DAP. Whether or not RIP2 RNA was present at 16 and 20 DAP could not be determined because its predicted position would be obscured by the signal from RIP1 RNA. The possibility that the band presumed to be RIP2 RNA represented neither RIP1 nor RIP2, but a third cross-hybridizing species has not been ruled out. However, the detection of only two RFLP loci with a RIP1 cDNA probe is consistent with the interpretation that the two bands represent the two maize RIPs.

EXAMPLE 9

Primer Extension Analysis of RIP1 and RIP2 Genes

To identify the site of transcriptional initiation of the RIP2 gene, and to better discriminate between the RIP1 and RIP2 transcripts, a primer extension analysis was performed as described in Asubel et al., supra, except as otherwise noted. The synthetic DNA oligonucleotide (5'GGTGCAGT-GTTTGATCAC3') and Hae III restriction fragments from the plasmid pBluescript were end-labeled with $^{32}P$ using T4 polynucleotide kinase according to manufacturer's instructions (New England Biolabs, Inc., Beverly, Ma.). RNA for use as internal controls in gel blots and primer extension assays was synthesized in vitro with the enzyme T3 RNA polymerase as instructed by the manufacturer (MEGAscript™ kit, Ambion, Inc., Austin, Tex.). The plasmid templates used were BamHI-digested pPST3 for synthesis of RIP2 RNA and XbaI-digested pZmcRIP-3 for synthesis of RIP1 RNA.

Following transcription, the DNA was removed by treatment with DNAseI, and the RNA was phase extracted with phenol/chloroform (1:1), ethanol precipitated, and redissolved in $H_2O$. RNA quality was determined by gel fractionation and ethidium bromide staining to confirm the presence of a single species of RNA (data not shown), and quantified by UV absorbance spectroscopy.

Figure 7:
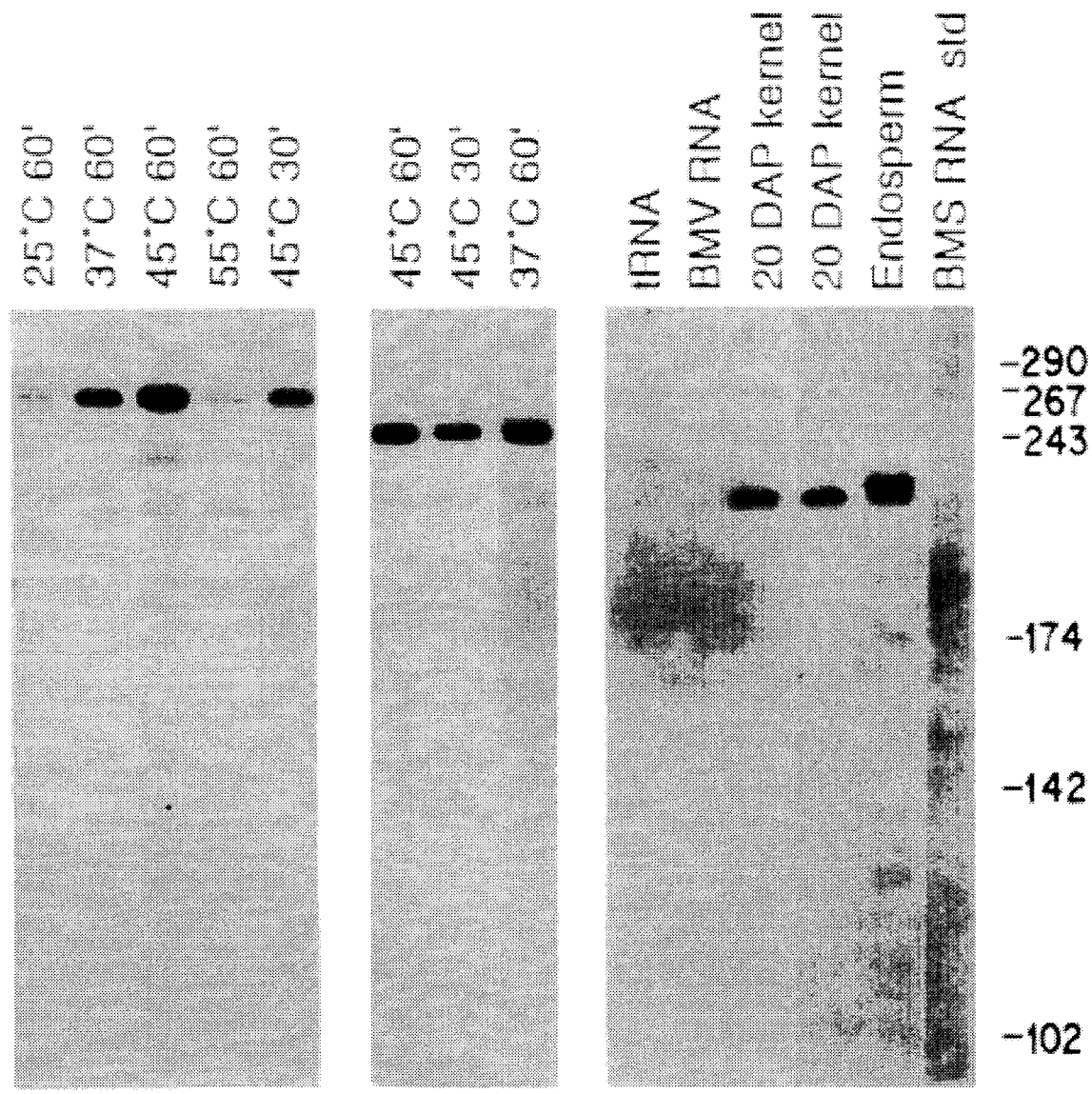

To optimize the assay, several experimental parameters were tested that might affect the specificity of extension products transcribed. The autoradiograph in FIG. 7 shows denaturing gel fractionation of primer extension products from positive control RNA (sections headed RIP2 and RIP1), negative control RNA (lanes tRNA and BMV), or maize RNA (lanes 20 DAP kernel, endosperm s.c., and BMS s.c.). The experimental variables are indicated above each lane. The extension product from the synthetic RIP2 RNA was predicted to be 275 nt based on the position of the restriction enzyme site at which the template plasmid for RNA synthesis was linearized. Using the RIP2 synthetic RNA for a template, the 45° C. primer extension reaction gave the strongest signal (RIP2 lane 45° C. 45 min). However, the relative amount of signal below the major extension products appeared to be greater in this lane than in the lane showing extension products from a 37° C. reaction (37° C. 60 min). A 55° C. primer extension reaction showed reduced amounts of the major extension products (RIP2 lane 55° C. 60 min). Therefore, based on the intensity of signal as well as the ratio of full length extension products to the smaller bands, the 37° C. 60 min primer extension reaction was considered to be the optimal reaction.

Synthetic RIP1 RNA (section headed RIP1) was also used as a substrate and the full length run off transcription product was predicted to be 245 nt. Of the three conditions tested, 45° C. 60 min, 45° C. 30 min, and 37° C. 45 min, the 37° C. reaction gave the optimal results based upon the same criteria discussed above. The specificity of the reaction for RIP RNA was demonstrated by primer extension reactions of control RNAs (tRNA and BMV) which showed no extension products.

Total RNA from maize kernels harvested at 20 DAP (lanes 20 DAP kernel) directed synthesis of a distinct extension product of approximately 210 nt. RNA from an endosperm suspension culture (Endosperm s.c.) showed two very closely migrating extension products, with the smaller of the two products comigrating with the products from kernel RNA. Reactions using RNA from BMS suspension cultures (BMS s.c.) contained no detectable RIP RNA as determined by the absence of extension products in that lane.

Figure 8:
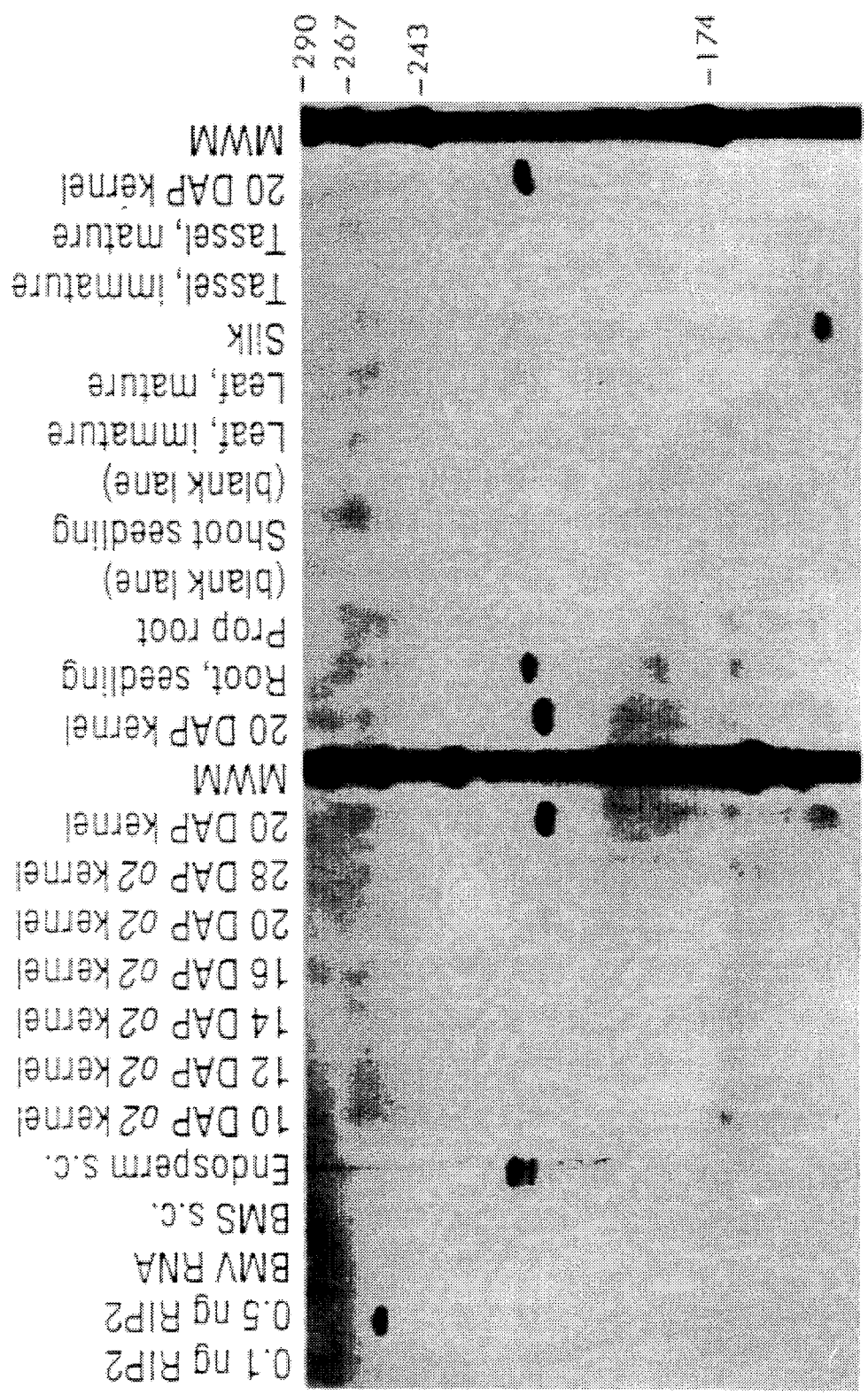

Once reaction conditions yielding specific primer extension products were established, RNAs from various parts of the plant were assayed for RIP RNA. The results of this experiment are presented in FIG. 8 with the sources of the RNA listed above the lanes. Primer extension reactions containing 0.1 and 0.5 ng of synthetic RNA from a RIP2 clone were included as controls and the resulting extension products are shown in the first two lanes (lanes 0.1 ng RIP2 and 0.5 ng RIP2). The presence of RIP RNA in roots was demonstrated by detection of a 216 nt band (lane Root, seedling). In addition to the lanes representing products from root RNA, the lanes showing products reverse transcribed from the RNA of leaf, silk, tassel, and endosperm suspension culture (lanes Leaf, immature; Leaf, mature; silk; tassel, mature; and Endosperm s.c.) also showed this 216 nt band. A slightly smaller band of 212 nt was visible in RNA isolated from developing kernels (lanes 20 DAP kernel, compare lanes 20 DAP kernel with Root, seedling). Additionally, the RNAs from 16 and 20 DAP opaque-2 kernels directed synthesis of the 212 nt extension products (lanes 16 DAP o2 kernel and 20 DAP o2 kernel). The only other lane showing the 212 nt extension product was that containing reaction products transcribed from RNA isolated from an endosperm culture (lane Endosperm s.c.). Only this reaction resulted in both the 212 and 216 nt bands, a result corresponding to that observed in FIG. 7.

The extensions products (212 nt) from kernel RNA were believed to be transcribed from the RIP1 RNA which is present at high levels in kernels harvested at 20 DAP (Bass et al., 1992). Consistent with this interpretation was the presence of the 212 nt products from the same RNAs shown to contain RIP1 RNA (ie., 16 and 20 DAP opaque-2 kernel RNA). The larger (216 nt) transcription products derived from reactions containing RNAs from root, silk, tassel, and endosperm culture are believed to result from RIP2 RNA. This assignment is consistent with the earlier observation that RNAs from these sources hybridized to the RIP2 RNA-specific probe RMA89 (FIG. 5).

EXAMPLE 10

RIP Activity of pRIP2-B6 RNA in vitro

The site-specific depurination of the large rRNA by RIPs can be monitored by gel electrophoresis of the purified RNA that has been treated with aniline. At an acidic pH, aniline induces strand scission at the point of depurination and generates a 3' terminal rRNA fragment of approximately 400 nt. To determine whether or not the lambdaRIP2 clone encoded a protein with RIP activity, rabbit reticulocyte translation extracts were programmed with synthetic RNA corresponding to the open reading frame region of RIP2.

Template plasmids (pPST3 and pPST7, described above) were linearized by digestion with Eco RI at a single site, and transcribed in vitro with T7 RNA Polymerass as instructed by the manufacturer (Epicentre Technologies, Madison, Wis.). The methods for purification and quantitation of synthetic RNAs are described above in Example 9. Aniline cleavage assays were performed on rabbit reticulocyte RNA from translation extracts as described by Bass et al., supra, unless specified otherwise below. L-methionine was substituted for radiolabeled L-methionine. Micrococcal nuclease treatment was performed according to the instructions supplied with the lysate (Promega). Synthetic or BMV RNAs were added to 20 μg/mL. Gelonin (Calbiochem) was added to 0.1 μg/mL. Reactions were for 45 min. at 30° C.

Figure 9:
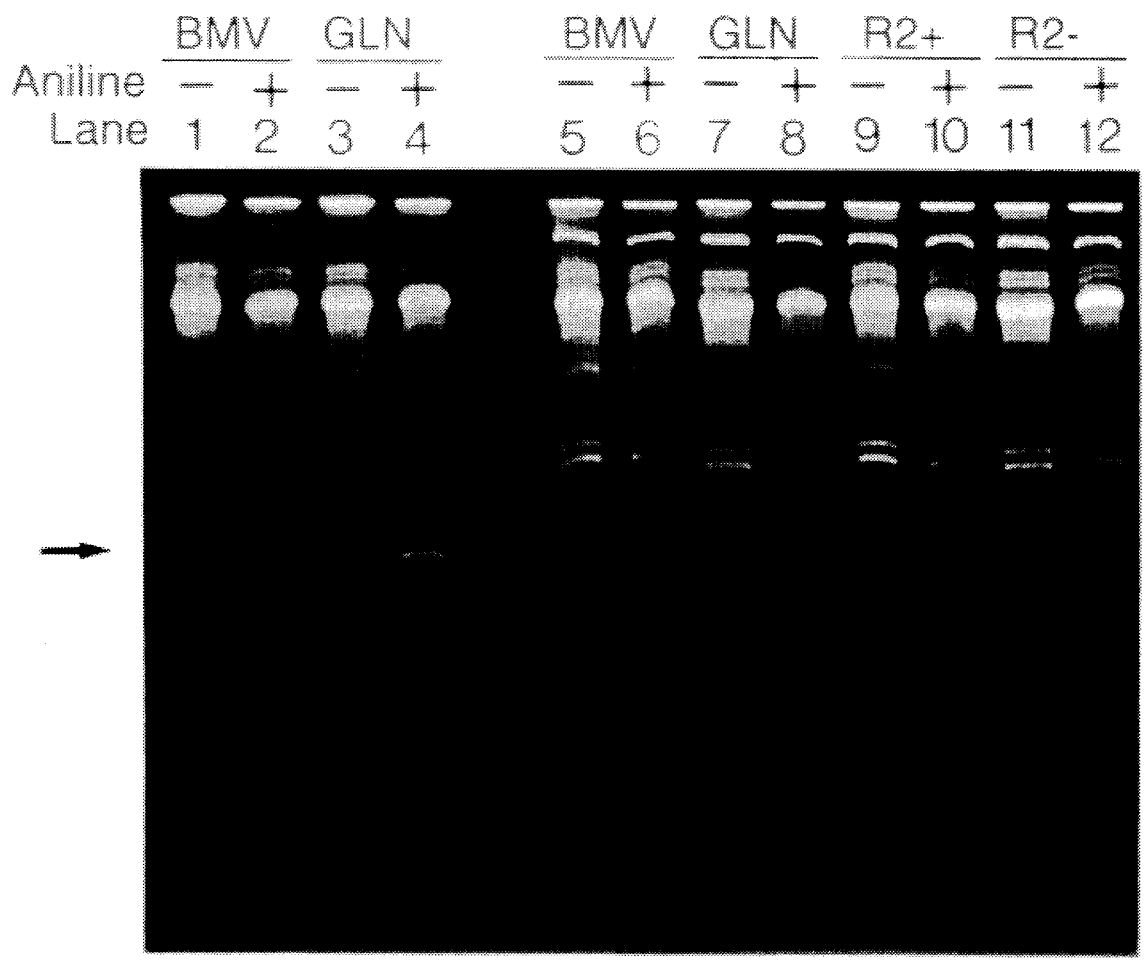

As shown in FIG. 9, RNA from translation extracts containing RIP2 coding strand RNA (lanes R2+) gave an aniline-dependent RNA fragment diagnostic for RIP activity (arrow). RNA from extracts plus either the RIP2 noncoding strand (lanes R2−) or BMV RNA (lanes BMV) did not show additional RNA fragments upon aniline treatment. For comparison, RNA from extracts treated with the commercially-available RIP, gelonin, showed the aniline-dependent RNA band (arrow).

In addition to the aniline-specific bands, several abundant RNA bands were observed (lanes 5–12). Their presence does not, however, affect the specificity of the RIP reaction assay. This is demonstrated by comparison of RNA from rabbit reticulocyte lysate that had not been treated with micrococcal nuclease (lanes 1–4). Rabbit reticulocyte lysate was incubated with control RNA (BMV lanes 1 and 2) and gelonin (GLN lanes 3 and 4). The band specific for RIP plus aniline treatment was the same size as that from lanes 8 and 10, which indicated the micrococcal nuclease treatment affected neither the specificity of the reaction nor the size of the 3' scission product. Additionally, this result indicated that the region of the large rRNA that is modified by RIPs was not a micrococcal nuclease hypersensitive site under the conditions of this experiment.

The foregoing examples are illustrative of the present invention, and are not to be construed as limiting thereof. The invention is defined by the following claims, with equivalents of the claims to be included therein.

That which is claimed is:

1. An isolated ribosome inactivating protein having the amino acid sequence of SEQ ID NO:2.

2. An agricultural composition comprising an effective ribosome-inhibiting protein of claim 1 in an agricultural carrier.

\* \* \* \* \*

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
( A ) LENGTH: 1934 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: CDS
( B ) LOCATION: 990..1826

( x i ) SEQUENCE DESCRIPTION: SEQ ID NO:1:

```
GTGCCAAGCT TTGAAAGAAG GATGTCAAAA GGCATTGGTG ATTGAACAAA GGCAGTCAAG      60

AGCCATTGAA AGAAAGTTGT ATGTTGAGAG CACTAAGACA ACGGTCTTAC AGTGTACAAA     120

ATATATCACT GAATAGTTAT ATCTTACTTT TTTAGCACTT GAGCAATTAA ACTTTTAGTT     180

GTTCATTGTT ATAGTCGATA CCCAGATATC ATACAGTGTC TAATATGAAC ATTTAATTTT     240

CATGTAATCA TTATGCTCTA ACATTTTTTC CCAAATAATG TGCTGTTGCA ACGACGGGCA     300

TCGTACTAGT AAAGTATATA TATATATATA TATATAGACT TTTACCATTC AAAAAAATTT     360

GAGGGCCTCA ATTTTTGTTT CGCCCCGGGT CCATGAAACC TAGGGACCGG CCGTGTATAT     420

ATATGGTCTT CCCTTCACTA ACTATATAGA GACAGATCAC ATCGGAATAA AAGAAATTTA     480

TAGACCAAAT CGGAAACCTA AAAACCAAAA ACCGAGCAAT TCGGTCTATT CGGTTTTAGT     540

TAGCAGGTTC AAAATGTCCG GTCCTACTAA TACTCAACAA TGATTAAGAA CCGATCTGCC     600

ATATTTTAAA AAAATTATGG ACCGGAATAA CACATAGCGA AAAGTTTAAG GAGCGAAAAT     660

ATTTTTTTTT CCTTGGCAAT TTGGACGGCA CGCGGAGACT GGCAGACCGC ATCCTCGTGA     720

AGCACGTTGT CCATGCCTGA AGAGAGTATT CTGTATTCGC AGTATTCCTG CATTTAAAAG     780

TTTGGTGAGC GAATCAATAA TTGGCATAAA TAATGCTACC GACGCATCAC CACATAGTAC     840

GTACCATAGT CATCCTTATC CTATCGAATT ACCTACATGC CCAACCCTCC CACTACATAT     900
```

-continued

| | | | | | | | | | | | | | | | | |
|---|---|---|---|---|---|---|---|---|---|---|---|---|---|---|---|---|
| ATCTGCAACG | AGCGCATCGC | CAATTCACAA | TGCCAATTGC | CAGCAACCCA | TCCATACTTT | | | | | | | | | | | 960 |

| CAGCTGTTGA | TACAAAAAGA | GAAGAGAGA | ATG<br>Met<br>1 | GCG<br>Ala | GAG<br>Glu | CCA<br>Pro | AAC<br>Asn | CCA<br>Pro<br>5 | GAG<br>Glu | TTG<br>Leu | 1013 |
|---|---|---|---|---|---|---|---|---|---|---|---|
| AGT<br>Ser | GGT<br>Gly<br>10 | CTT<br>Leu | ATT<br>Ile | ACT<br>Thr | CAA<br>Gln | ACA<br>Thr<br>15 | AAG<br>Lys | AAG<br>Lys | AAA<br>Lys | AAT<br>Asn | ATA<br>Ile | GTG<br>Val<br>20 | CCA<br>Pro | AAG<br>Lys | TTC<br>Phe | 1061 |
| ACC<br>Thr<br>25 | GAA<br>Glu | ATC<br>Ile | TTC<br>Phe | CCC<br>Pro | GTG<br>Val<br>30 | GAG<br>Glu | GAC<br>Asp | ACG<br>Thr | GCC<br>Ala | TAC<br>Tyr<br>35 | CCT<br>Pro | TAC<br>Tyr | AGC<br>Ser | GCC<br>Ala | TTC<br>Phe<br>40 | 1109 |
| ATC<br>Ile | ACC<br>Thr | TCC<br>Ser | GTC<br>Val | CGG<br>Arg<br>45 | AAA<br>Lys | GAA<br>Glu | GTG<br>Val | ATC<br>Ile | AAA<br>Lys<br>50 | TAC<br>Tyr | TGC<br>Cys | ACC<br>Thr | AAC<br>Asn | CAT<br>His<br>55 | ACA<br>Thr | 1157 |
| GGC<br>Gly | ATC<br>Ile | GTC<br>Val | CAG<br>Gln<br>60 | CCC<br>Pro | GTG<br>Val | CTG<br>Leu | CCG<br>Pro | CTG<br>Leu<br>65 | GAG<br>Glu | AAG<br>Lys | AAT<br>Asn | GTC<br>Val | CCC<br>Pro<br>70 | GAG<br>Glu | CTC<br>Leu | 1205 |
| TGG<br>Trp | TTC<br>Phe | TAC<br>Tyr<br>75 | ACC<br>Thr | GAG<br>Glu | CTC<br>Leu | AAA<br>Lys | ACG<br>Thr<br>80 | AAG<br>Lys | ACC<br>Thr | AGG<br>Arg | TCC<br>Ser | ATC<br>Ile<br>85 | ACG<br>Thr | CTC<br>Leu | GCC<br>Ala | 1253 |
| ATA<br>Ile | CGT<br>Arg<br>90 | ATG<br>Met | GAC<br>Asp | AAC<br>Asn | CTC<br>Leu | TAC<br>Tyr<br>95 | CTG<br>Leu | GTC<br>Val | GGC<br>Gly | TTC<br>Phe | AGG<br>Arg<br>100 | ACC<br>Thr | CCC<br>Pro | GGC<br>Gly | GGG<br>Gly | 1301 |
| GTG<br>Val<br>105 | TGG<br>Trp | TGG<br>Trp | GAG<br>Glu | TTC<br>Phe | GGC<br>Gly<br>110 | AAG<br>Lys | GAC<br>Asp | GGC<br>Gly | GAC<br>Asp | ACC<br>Thr<br>115 | CAC<br>His | CTC<br>Leu | CTC<br>Leu | GAC<br>Asp | GAC<br>Asp<br>120 | 1349 |
| AAC<br>Asn | GCC<br>Ala | AAG<br>Lys | TGG<br>Trp | CTC<br>Leu<br>125 | GGC<br>Gly | TTT<br>Phe | GGC<br>Gly | GGC<br>Gly | CGG<br>Arg<br>130 | TAC<br>Tyr | CAG<br>Gln | GAC<br>Asp | CTC<br>Leu | ATC<br>Ile<br>135 | GGC<br>Gly | 1397 |
| AGT<br>Ser | AAG<br>Lys | GGC<br>Gly | CTG<br>Leu<br>140 | GAG<br>Glu | ACC<br>Thr | GTC<br>Val | ACC<br>Thr | ATG<br>Met<br>145 | GGC<br>Gly | CGT<br>Arg | GCC<br>Ala | GAA<br>Glu | ATG<br>Met<br>150 | ACC<br>Thr | ACG<br>Thr | 1445 |
| GCC<br>Ala | GTC<br>Val | AAC<br>Asn<br>155 | TAC<br>Tyr | CTG<br>Leu | GCG<br>Ala | AAG<br>Lys | AAG<br>Lys<br>160 | ACG<br>Thr | ACG<br>Thr | ACG<br>Thr | ACA<br>Thr | CTA<br>Leu<br>165 | GCA<br>Ala | GAG<br>Glu | GCG<br>Ala | 1493 |
| GCG<br>Ala | GAG<br>Glu | GAG<br>Glu<br>170 | GAG<br>Glu | GAG<br>Glu | GAG<br>Glu | CTG<br>Leu | CTG<br>Leu<br>175 | CTG<br>Leu | CTG<br>Leu | CAG<br>Gln | GCA<br>Ala | GCG<br>Ala<br>180 | GCT<br>Ala | GAC<br>Asp | CCC<br>Pro | 1541 |
| AAA<br>Lys<br>185 | GCC<br>Ala | GAG<br>Glu | GAG<br>Glu | AAG<br>Lys | AGC<br>Ser<br>190 | AAC<br>Asn | CTG<br>Leu | GCG<br>Ala | AAG<br>Lys | CTA<br>Leu<br>195 | GTG<br>Val | ATC<br>Ile | ATG<br>Met | GTA<br>Val | TGC<br>Cys<br>200 | 1589 |
| GAG<br>Glu | GGG<br>Gly | CTG<br>Leu | CGG<br>Arg | TTC<br>Phe<br>205 | TTC<br>Phe | ACC<br>Thr | GTG<br>Val | TCC<br>Ser | CGC<br>Arg<br>210 | AAG<br>Lys | GTA<br>Val | GAC<br>Asp | GAG<br>Glu | GGG<br>Gly<br>215 | TTC<br>Phe | 1637 |
| AAG<br>Lys | AAG<br>Lys | CCG<br>Pro | CAA<br>Gln<br>220 | GCG<br>Ala | GTG<br>Val | ACC<br>Thr | ATA<br>Ile | TCG<br>Ser<br>225 | GCG<br>Ala | CTG<br>Leu | GAG<br>Glu | GGG<br>Gly | AAG<br>Lys<br>230 | CAG<br>Gln | GTG<br>Val | 1685 |
| CAG<br>Gln | AAA<br>Lys | TGG<br>Trp<br>235 | GAC<br>Asp | AGG<br>Arg | ATC<br>Ile | TCG<br>Ser | AAA<br>Lys<br>240 | GCC<br>Ala | GTC<br>Val | TTC<br>Phe | AGG<br>Arg | TGG<br>Trp<br>245 | GCC<br>Ala | GTC<br>Val | GAC<br>Asp | 1733 |
| CCG<br>Pro | ACC<br>Thr<br>250 | GCT<br>Ala | GAG<br>Glu | ATC<br>Ile | CCC<br>Pro | GAC<br>Asp<br>255 | ATG<br>Met | AAG<br>Lys | GAT<br>Asp | CTT<br>Leu | GGC<br>Gly<br>260 | ATC<br>Ile | AAA<br>Lys | GAT<br>Asp | AAA<br>Lys | 1781 |
| AAC<br>Asn<br>265 | GCA<br>Ala | GCA<br>Ala | GCG<br>Ala | CAG<br>Gln | ATC<br>Ile<br>270 | GTT<br>Val | GCG<br>Ala | CTC<br>Leu | GTT<br>Val | AAG<br>Lys<br>275 | GAC<br>Asp | CAA<br>Gln | AAC<br>Asn | TAGTACTGCT | | 1833 |

| GCTACTACTA | CGTATGAGAA | CAAGGAGGAG | TTCTCTGATG | ATGATACACA | CATCAAGACT | 1893 |
|---|---|---|---|---|---|---|
| TGTTTGTTGC | TCTACTTCCA | CGTGGTACAG | TAGCAGTATA | C | | 1934 |

5,552,140

( 2 ) INFORMATION FOR SEQ ID NO:2:

( i ) SEQUENCE CHARACTERISTICS:
        ( A ) LENGTH: 278 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Ala Glu Pro Asn Pro Glu Leu Ser Gly Leu Ile Thr Gln Thr Lys
 1               5                  10                  15

Lys Lys Asn Ile Val Pro Lys Phe Thr Glu Ile Phe Pro Val Glu Asp
            20                  25                  30

Thr Ala Tyr Pro Tyr Ser Ala Phe Ile Thr Ser Val Arg Lys Glu Val
        35                  40                  45

Ile Lys Tyr Cys Thr Asn His Thr Gly Ile Val Gln Pro Val Leu Pro
     50                  55                  60

Leu Glu Lys Asn Val Pro Glu Leu Trp Phe Tyr Thr Glu Leu Lys Thr
 65                  70                  75                  80

Lys Thr Arg Ser Ile Thr Leu Ala Ile Arg Met Asp Asn Leu Tyr Leu
                 85                  90                  95

Val Gly Phe Arg Thr Pro Gly Gly Val Trp Trp Glu Phe Gly Lys Asp
            100                 105                 110

Gly Asp Thr His Leu Leu Asp Asp Asn Ala Lys Trp Leu Gly Phe Gly
            115                 120                 125

Gly Arg Tyr Gln Asp Leu Ile Gly Ser Lys Gly Leu Glu Thr Val Thr
    130                 135                 140

Met Gly Arg Ala Glu Met Thr Thr Ala Val Asn Tyr Leu Ala Lys Lys
145                 150                 155                 160

Thr Thr Thr Thr Leu Ala Glu Ala Ala Glu Glu Glu Glu Glu Leu Leu
                165                 170                 175

Leu Leu Gln Ala Ala Ala Asp Pro Lys Ala Glu Glu Lys Ser Asn Leu
            180                 185                 190

Ala Lys Leu Val Ile Met Val Cys Glu Gly Leu Arg Phe Phe Thr Val
            195                 200                 205

Ser Arg Lys Val Asp Glu Gly Phe Lys Lys Pro Gln Ala Val Thr Ile
    210                 215                 220

Ser Ala Leu Glu Gly Lys Gln Val Gln Lys Trp Asp Arg Ile Ser Lys
225                 230                 235                 240

Ala Val Phe Arg Trp Ala Val Asp Pro Thr Ala Glu Ile Pro Asp Met
                245                 250                 255

Lys Asp Leu Gly Ile Lys Asp Lys Asn Ala Ala Ala Gln Ile Val Ala
            260                 265                 270

Leu Val Lys Asp Gln Asn
            275
```

( 2 ) INFORMATION FOR SEQ ID NO:3:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..54

( x i ) SEQUENCE DESCRIPTION: SEQ ID NO:3:

```
ACG  ACA  CTA  GCA  GAG  GCG  GCG  GAG  GAG  GAG  GAG  GAG  CTG  CTG  CTG  CTG         48
Thr  Thr  Leu  Ala  Glu  Ala  Ala  Glu  Glu  Glu  Glu  Glu  Leu  Leu  Leu  Leu
 1              5                        10                       15

CAG  GCA                                                                                54
Gln  Ala
```

( 2 ) INFORMATION FOR SEQ ID NO:4:

( i ) SEQUENCE CHARACTERISTICS:
        ( A ) LENGTH: 18 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Thr  Thr  Leu  Ala  Glu  Ala  Ala  Glu  Glu  Glu  Glu  Glu  Leu  Leu  Leu  Leu
 1              5                        10                       15

Gln  Ala
```

( 2 ) INFORMATION FOR SEQ ID NO:5:

( i ) SEQUENCE CHARACTERISTICS:
        ( A ) LENGTH: 75 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..75

( x i ) SEQUENCE DESCRIPTION: SEQ ID NO:5:

```
ATG  GCG  ACA  CTG  GAG  GAG  GAG  GAG  GTG  AAG  ATG  CAG  ATG  CAG  ATG  CCG         48
Met  Ala  Thr  Leu  Glu  Glu  Glu  Glu  Val  Lys  Met  Gln  Met  Gln  Met  Pro
 1              5                        10                       15

GAG  GCC  GCT  GAT  CTG  GCG  GCG  GCG  GCA                                             75
Glu  Ala  Ala  Asp  Leu  Ala  Ala  Ala  Ala
               20                       25
```

( 2 ) INFORMATION FOR SEQ ID NO:6:

( i ) SEQUENCE CHARACTERISTICS:
        ( A ) LENGTH: 25 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Met  Ala  Thr  Leu  Glu  Glu  Glu  Glu  Val  Lys  Met  Gln  Met  Gln  Met  Pro
 1              5                        10                       15

Glu  Ala  Ala  Asp  Leu  Ala  Ala  Ala  Ala
               20                       25
```